United States Patent
Spottiswoode et al.

(10) Patent No.: US 10,264,994 B2
(45) Date of Patent: Apr. 23, 2019

(54) FREE BREATHING MOTION CORRECTED PIXEL-WISE MRI MYOCARDIAL T1 PARAMETER MAPPING

(71) Applicants: Siemens Healthcare Gmbh, Erlangen OT (DE); The United States of America, as represented by the Secretary, Department of Health and Human Services, Washington, DC (US)

(72) Inventors: Bruce S. Spottiswoode, Chicago, IL (US); Peter Kellman, Bethesda, MD (US)

(73) Assignees: Siemens Healthcare GmbH, Erlangen (DE); The United States of America, as represented by the Secretary, Department of Health and Human Services, Washington, DC (US)

( * ) Notice: Subject to any disclaimer, the term of this patent is extended or adjusted under 35 U.S.C. 154(b) by 362 days.

(21) Appl. No.: 15/155,205

(22) Filed: May 16, 2016

(65) Prior Publication Data
US 2017/0325707 A1 Nov. 16, 2017

(51) Int. Cl.
*G01R 33/56* (2006.01)
*A61B 5/055* (2006.01)
(Continued)

(52) U.S. Cl.
CPC .......... *A61B 5/055* (2013.01); *A61B 5/0044* (2013.01); *A61B 5/7214* (2013.01); *G01R 33/50* (2013.01);
(Continued)

(58) Field of Classification Search
CPC ............ G01R 33/4816; G01R 33/4818; G01R 33/482; G01R 33/4822; G01R 33/4824;
(Continued)

(56) References Cited

U.S. PATENT DOCUMENTS

| 2013/0119985 A1* | 5/2013 | Lin | G01R 33/4818 324/309 |
| 2014/0077807 A1* | 3/2014 | Edelman | G01R 33/5635 324/309 |
| 2015/0077106 A1* | 3/2015 | Kim | G01R 33/4828 324/309 |

OTHER PUBLICATIONS

Akcakaya, et al., "On the Selection of Sampling Points for Myocardial T1 Mapping", Magnetic Resonance in Medicine 00:00-00 (2014) 13 pages.
(Continued)

*Primary Examiner* — Tung X Nguyen

(57) ABSTRACT

A method for performing free breathing pixel-wise myocardial T1 parameter mapping includes performing a free-breathing scan of a cardiac region at a plurality of varying saturation recovery times to acquire a k-space dataset; generating an image dataset based on the k-space dataset; and performing a respiratory motion correction process on the image dataset. The respiratory motion correction process comprises selecting a target image from the image dataset, co-registering each image in the image dataset to the target image to determine a spatial alignment measurement for each image, and identifying a subset of the image dataset comprising images with the spatial alignment measurement above a predetermined value. Following the respiratory motion correction process, a pixel-wise fitting is performed on the image dataset to estimate T1 relaxation time values for the cardiac region. Then, a pixel-map of the cardiac region is produced depicting the T1 relaxation time values.

21 Claims, 6 Drawing Sheets

(51) Int. Cl.
  G01R 33/565 (2006.01)
  A61B 5/00 (2006.01)
  G01R 33/50 (2006.01)
  A61B 5/08 (2006.01)
  A61B 5/145 (2006.01)
  G01R 33/567 (2006.01)

(52) U.S. Cl.
  CPC ... G01R 33/5602 (2013.01); G01R 33/56509 (2013.01); *A61B 5/0816* (2013.01); *A61B 5/14535* (2013.01); *A61B 2576/023* (2013.01); *G01R 33/5608* (2013.01); *G01R 33/5673* (2013.01)

(58) Field of Classification Search
  CPC ............ G01R 33/4826; G01R 33/4828; G01R 33/483; G01R 33/4831; G01R 33/4833; G01R 33/4835
  See application file for complete search history.

(56) References Cited

OTHER PUBLICATIONS

Mehmet Akçakaya, Sebastian Weingärtner, Tamer A Basha, Sébastien Roujol, Reza Nezafat Journal of Cardiovascular Magnetic Resonance 2015, 17(Suppl 1):Q1 (Feb. 3, 2015).

Blume, U., Lockie, T., Stehning, C., Sinclair, S., Uribe, S., Razavi, R. and Schaeffter, T. (2009), Interleaved T1 and T2 relaxation time mapping for cardiac applications. J. Magn. Reson. Imaging, 29: 480-487. doi:10.1002/jmri.21652.

Chow, Kelvin, et al. "Saturation recovery single-shot acquisition (SASHA) for myocardial T1 mapping." Magnetic resonance in medicine 71.6 (2014): 2082-2095.

Grgac, Ksenija, Peter Zijl, and Qin Qin. "Hematocrit and oxygenation dependence of blood 1H2O T1 at 7 tesla." Magnetic resonance in medicine 70.4 (2013): 1153-1159.

Kellman, Peter, and Michael S. Hansen. "T1-mapping in the heart: accuracy and precision." Journal of cardiovascular magnetic resonance 16.1 (2014): 1.

Kvernby, Sofia, et al. "Simultaneous three-dimensional myocardial T1 and T2 mapping in one breath hold with 3D-QALAS." Journal of Cardiovascular Magnetic Resonance 16.1 (2014): 1.

Markl, M., M. T. Alley, and N. J. Pelc. "Balanced phase-contrast steady-state free precession (PC-SSFP): A novel technique for velocity encoding by gradient inversion." Magnetic resonance in medicine 49.5 (2003): 945-952.

Messroghli, Daniel R., et al. "Modified Look-Locker Inversion recovery (MOLLI) for high-resolution T1 mapping of the heart." Magnetic resonance in medicine 52.1 (2004): 141-146.

Piechnik, Stefan K., et al. "Shortened Modified Look-Locker Inversion recovery (ShMOLLI) for clinical myocardial T1-mapping at 1.5 and 3 T within a 9 heartbeat breathhold." Journal of cardiovascular magnetic resonance 12.1 (2010): 1.

Weingärtner, Sebastian, et al. "Combined saturation/inversion recovery sequences for improved evaluation of scar and diffuse fibrosis in patients with arrhythmia or heart rate variability." Magnetic resonance in medicine 71.3 (2014): 1024-1034.

Weingärtner, Sebastian, et al. "Free-breathing multislice native myocardial T1 mapping using the slice-interleaved T1 (STONE) sequence." Magnetic resonance in medicine 74.1 (2015): 115-124.

\* cited by examiner

1

FREE BREATHING MOTION CORRECTED PIXEL-WISE MRI MYOCARDIAL T1 PARAMETER MAPPING

TECHNOLOGY FIELD

The present invention relates generally to methods, systems, and apparatuses for performing myocardial T1 parameter mapping during magnetic resonance imaging using a free-breathing scan.

BACKGROUND

Quantitative T1 mapping of the myocardium is useful clinically in the pre-contrast (native) scenario since an increase in T1 is associated with edema or protein deposition, whereas a reduced T1 is associated with lipid or iron deposition. T1 maps from both pre and post-contrast scenarios can be used to quantitatively estimate the volume of contrast agent in the extracellular space, which is indicative of edema, fibrotic scar, or diffuse fibrosis.

Myocardial T1 parameter mapping typically involves inversion or saturation prepared imaging, followed by a series of readouts to sample the T1 recovery. These readouts occur at a specific cardiac phase over multiple heartbeats. They most commonly involve single-shot scans and are acquired over a breath hold for a single slice location. The introduction of navigator gating allows one to scan during free breathing, thus enabling segmented and/or multi-slice acquisitions.

A challenge with T1 mapping during free breathing is that the T1 for myocardium is to the order of 1 second, so the commonly used inversion-prepared T1 mapping techniques require a delay of 8-10 seconds for full signal recovery before a subsequent inversion pulse. Performing inversion prepared T1 mapping during free breathing thus becomes inefficient because of these long compulsory recovery periods after each inversion pulse. Interleaved acquisitions across multiple slices can be performed to improve efficiency, but such approaches are only more efficient for the acquisition of multiple non-overlapping slices, which isn't practical for some cardiac views. Saturation recovery based T1 mapping resets the magnetization after each saturation pulse so these images can be acquired more efficiently, making the technique more suitable for free breathing approaches.

It is also possible to extend the saturation recovery T1 mapping technique to additionally obtain a co-registered T2 map in the same scan. Quantitative T2 mapping is useful for assessing conditions such as acute ischemia, myocarditis and heart transplant rejection, which alter the myocardial water content and consequently prolong the T2 relaxation times. Simultaneous T1 and T2 mapping may be additionally useful, for example, to estimate blood saturation and hematocrit, or to create synthetic images with any desired T1 or T2 weighting.

Myocardial T2 mapping may be achieved by applying multiple T2 preparation pulses prior to the readout to introduce varying levels of T2-dependent signal. Similar to T1 mapping, single shot readouts over multiple heartbeats can be used to obtain images suitable for pixel-wise fitting. Combined T1 and T2 mapping can be achieved by adding varying T2 preparations between the saturation pulse and the readout, and fitting both T1 and T2 using Bloch equations of the signal evolution. Saturation recovery and T2 preparation has previously been combined to perform simultaneous T1 and T2 mapping, but only in a breath hold scenario.

SUMMARY

Embodiments of the present invention address and overcome one or more of the above shortcomings and drawbacks, by providing methods, systems, and apparatuses related to for performing myocardial T1 parameter mapping during magnetic resonance imaging using a free-breathing scan. Motion correction during free breathing offers a simpler workflow than navigated scans, and provides an elegant framework for improving signal-to-noise and measurement precision.

According to some embodiments, a method for performing free breathing pixel-wise myocardial T1 parameter mapping includes performing a free-breathing scan of a cardiac region at a plurality of varying saturation recovery times to acquire a k-space dataset; generating an image dataset based on the k-space dataset; and performing a respiratory motion correction process on the image dataset. In some embodiments, the k-space dataset of the cardiac region comprises a plurality of redundant datasets for each of the plurality of varying saturation recovery times. The respiratory motion correction process comprises selecting a target image from the image dataset, co-registering each image in the image dataset to the target image to determine a spatial alignment measurement for each image, and identifying a subset of the image dataset comprising images with the spatial alignment measurement above a predetermined value. Following the respiratory motion correction process, a pixel-wise fitting is performed on the image dataset to estimate T1 relaxation time values for the cardiac region. Then, a pixel-map of the cardiac region is produced depicting the T1 relaxation time values.

Various techniques may be used for performing the pixel-wise fitting in the aforementioned method. For example, in some embodiments, the pixel-wise fitting performs a variable order parameter fit using parameters comprising a full longitudinal magnetization value, a T1 value, and a bias term value. In other embodiments, the pixel-wise fitting performs a 2 parameter fit using a full longitudinal magnetization value and a T1 value. In still other embodiments, pixel-wise fitting performs a 4 parameter fit using parameters comprising a full longitudinal magnetization value, a T1 value, a T2 value, and a bias term value.

In some embodiments of the aforementioned method, the free-breathing scan is performed using a saturation recovery T1 sampling strategy which applies a sequence comprising a saturation pulse and a readout repeated over multiple heartbeats. The aforementioned method may further include the features of modifying a gradient associated with the readout to enhance phase differences between flowing blood and stationary myocardium in the cardiac region; generating a phase map based on the phase differences; using the phase map in addition to the corresponding magnitude images to improve image co-registration. Additionally, each sequence may further comprise a T2 preparation pulse of variable duration inserted between the saturation pulse and the readout, and the aforementioned method further comprises extending the pixel-wise fitting on the image dataset to additionally estimate T2 relaxation time values for the cardiac region; and producing a second pixel-map of the cardiac region depicting the T2 relaxation time values. In one embodiment, the T2 preparation pulse is introduced immediately prior to the readout. Additionally, the T2 preparation pulse duration may be kept constant to improve contrast between blood and myocardium.

According to other embodiments, an article of manufacture for performing free breathing pixel-wise myocardial T1 parameter mapping comprises a non-transitory, tangible computer-readable medium holding computer-executable instructions for performing the aforementioned method, with or without the additional features set out above.

According to other embodiments, a system for performing free breathing pixel-wise myocardial T1 parameter mapping includes a magnetic resonance imaging scanner and a computer. The magnetic resonance imaging scanner is configured to perform a free-breathing scan of a cardiac region at a plurality of varying saturation recovery times to acquire a k-space dataset. The computer comprises an image data processor which is configured to generate an image dataset based on the k-space dataset and perform a respiratory motion correction process on the image dataset. This respiratory motion correction process includes selecting a target image from the image dataset, co-registering each image in the image dataset to the target image to determine a spatial alignment measurement for each image, and identifying a subset of the image dataset comprising images with the spatial alignment measurement above a predetermined value. The image data processor is further configured to perform a pixel-wise fitting on the image dataset following the respiratory motion correction process to estimate T1 relaxation time values for the cardiac region. Then, a pixel-map of the cardiac region may be produced depicting the T1 relaxation time values.

In some embodiments of the aforementioned system, the magnetic resonance imaging scanner is further configured to apply a plurality of T2 preparation pulses of variable duration between saturation pulses and readouts during the free-breathing scan of the cardiac region. In these embodiments, the image data processor may be further configured to extend the pixel-wise fitting on the image dataset to additionally estimate the T2 relaxation time values for the cardiac region and produce a second pixel-map of the cardiac region depicting the T2 relaxation time values.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses related to performing free breathing pixel-wise myocardial T1 parameter mapping. More specifically, the techniques described herein acquire co-registered pixel-wise T1 parameter maps of the heart from a single free breathing sequence, and without the use of a navigator. Saturation recovery imaging is used since it provides more flexibility for a free breathing scan, and elastic image registration can be used to correct for respiratory motion. T1 (and optional co-registered T2) maps are then obtained from the spatially aligned images using non-linear pixel-wise fitting. As described in further detail below, the saturation recovery T1 sampling strategy is performed with repeated saturation times and recovery heartbeats. The repeats ensure redundant data which can be discarded if there is spatial misalignment due to respiratory position. Additionally, non-rigid motion correction is performed to correct for minor spatial misalignment. The resulting deformation fields are used to identify images with major spatial misalignment which are discarded. In some embodiments, T2-preparation between the saturation pulse and the readout, or the integration of motion sensitized phase images, can be used for improved motion correction. The former case also facilitates combined free breathing T1 and T2 myocardial parameter mapping.

Figure 1:
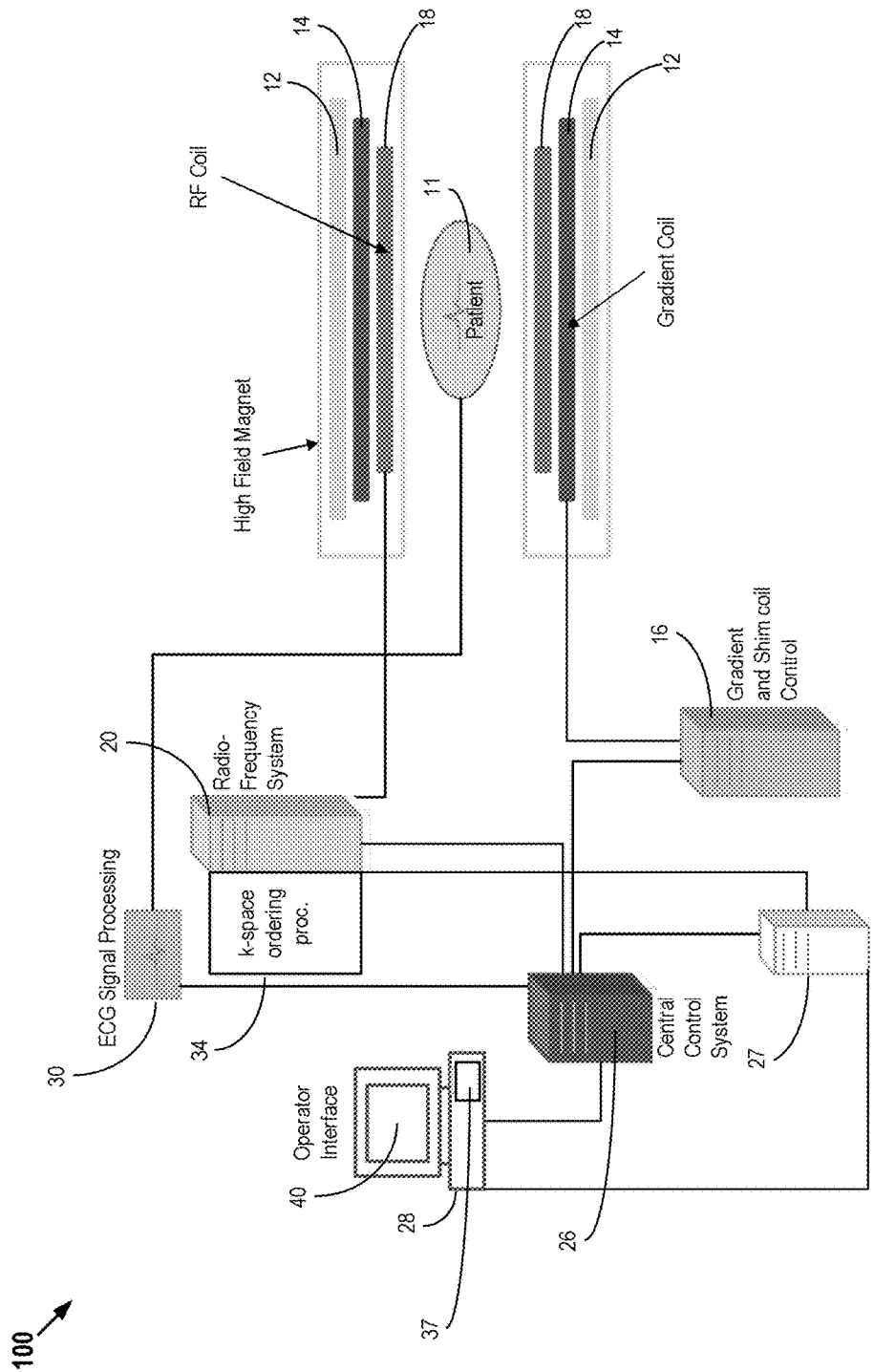
FIG. 1 shows a system for ordering acquisition of frequency domain components representing magnetic resonance image data for storage in a k-space storage array, as used by some embodiments of the present invention.

FIG. 1 shows a system 100 for ordering acquisition of frequency domain components representing magnetic resonance imaging (MRI) data for storage in a k-space storage array, as used by some embodiments of the present invention. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MRI device magnetic field resulting from patient anatomical variation and other sources. The magnetic field gradients include a slice-selection gradient magnetic field, a phase-encoding gradient magnetic field and a readout gradient magnetic field that are applied to patient 11.

Further radio frequency (RF) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body as they return to an equilibrium position established by the static and gradient magnetic fields. The magnetic resonance signals are detected and processed by a detector within RF module 20 and k-space component processor unit 34 to provide a magnetic resonance dataset to an image data processor for processing into an image. In some embodiments, the image data processor is located in central control unit 26. However, in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising a magnetic resonance dataset. The k-space array of individual data elements has a designated center and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components are sequentially acquired during acquisition of a magnetic resonance dataset representing a magnetic resonance image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components is substantially minimized.

Central control unit 26 uses information stored in an internal database to process the detected magnetic resonance signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Continuing with reference to FIG. 1, display processor 37 processes the magnetic resonance signals to reconstruct one or more images for presentation on display 40, for example. Various techniques generally known in the art may be used for reconstruction.

Figure 2:
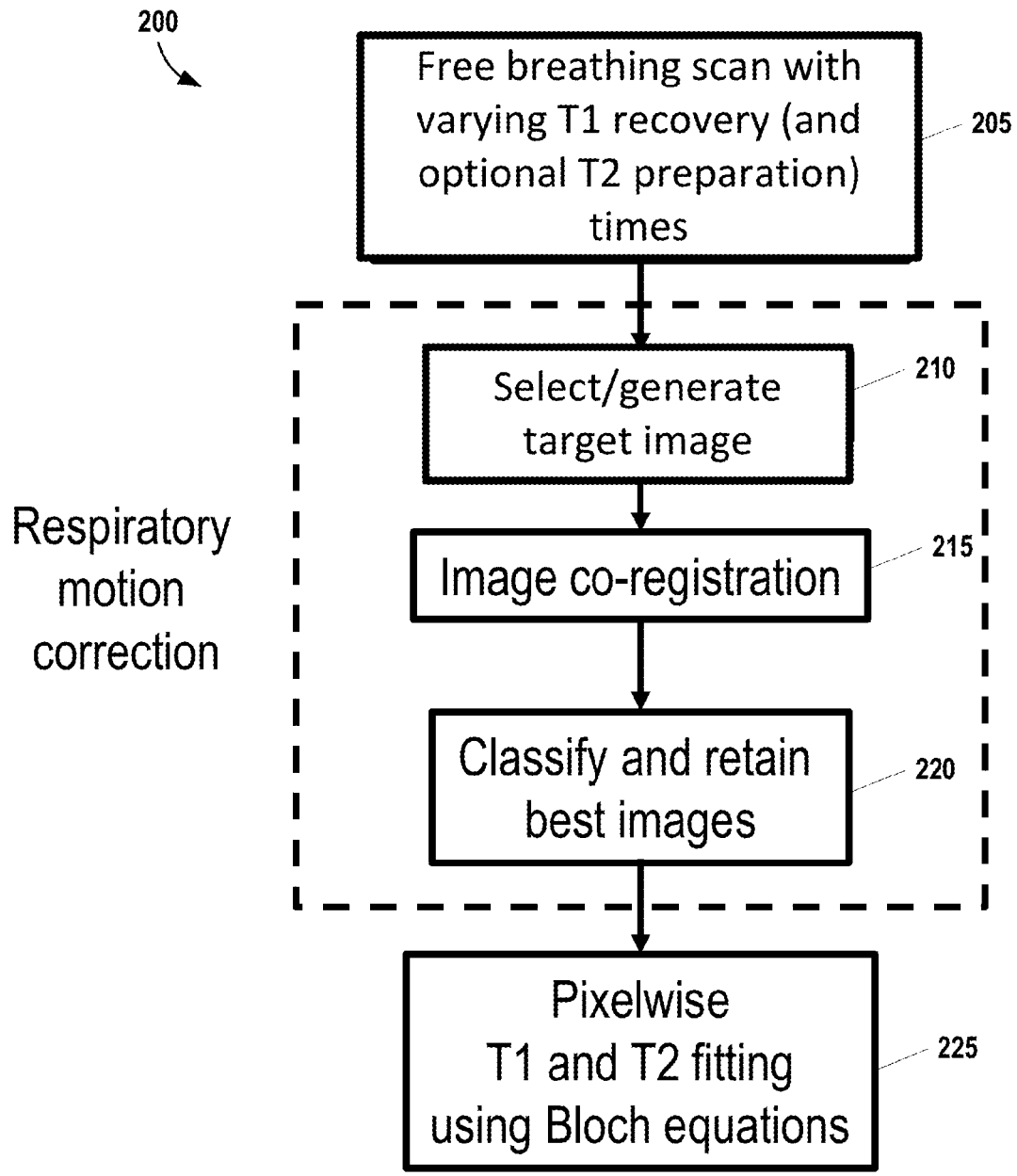
FIG. 2 presents an example process for T1 mapping during free breathing, according to some embodiments.
Figure 3A:
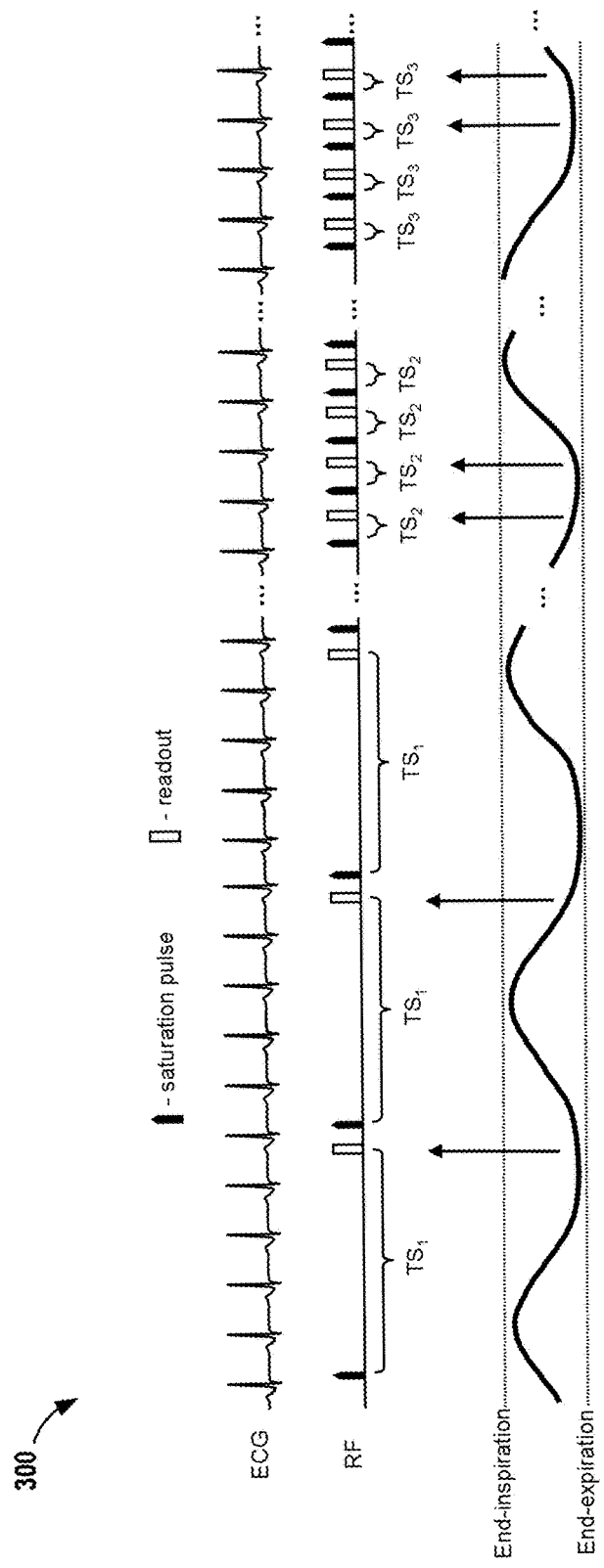
FIG. 3A shows an acquisition strategy where T1 mapping may be performed, according to some embodiments.

FIG. 2 presents an example process 200 for T1 mapping during free breathing, according to some embodiments. The process starts at step 205 where a free-breathing scan is performed (e.g., using system 100 shown in FIG. 1). In this example, images are acquired during free breathing at multiple saturation recovery times (TS), providing samples at multiple points along the T1 recovery curve. Sample points at a particular saturation time are repeated to ensure sufficient redundancy that images at all saturation times are available at a similar position in the respiratory cycle for reliable co-registration. FIG. 3A shows an acquisition strategy 300 that may be employed in some embodiments. In this example, acquisitions at a specific saturation time are repeated to ensure that images at a similar respiratory phase are available for co-registration (as shown by the arrows).

Continuing with reference to FIG. 2, respiratory motion correction is performed at steps 210-220. At step 210, a target image is selected. This target image may be selected, for example by (a) spatially averaging all images to generate a template; (b) using a brute-force approach whereby all images are registered to each other and the deformation fields (or registration residuals) are used to reveal the most representative target image; or (c) using approaches (a) or (b) only with the images with longest saturation time, where the contrast between blood and myocardium will be most pronounced. Elastic motion correction is next performed at step 215 to co-register all images to the target image. Techniques for elastic motion correction are generally known in the art and, in principle, any conventional technique may be employed at step 215. Briefly, "elastic" or "non-rigid" registration refers to a class of methods where the images to be registered have nonlinear geometric differences. These methods involve locally warping the image to align with the target image selected at 210. Examples of elastic registration techniques that may be applied at step 215 include, without limitation, radial basis functions such as thin-plate or surface splines, multiquadrics, and compactly-supported transformations. Following image co-registration, at step 220, images with poor spatial alignment are discarded. There are few enough images that the optimal target for co-registration could be obtained in a reasonable time using a brute force approach, whereby all image co-registration options are performed.

Once a spatially aligned subset of images is selected, pixel-wise curve fitting is performed at step 225 using Bloch Equations to estimate the relaxation time parameter to produce a pixel-map of T1. The fit performed at step 225 can be based on 2 or 3 parameters. More than 3 sample points (or TS times) are required for reliable 3 parameter fitting. An initial fully recovered anchor image, can be acquired, but may not be used for the fit depending on its location in the respiratory cycle.

Figure 3B:
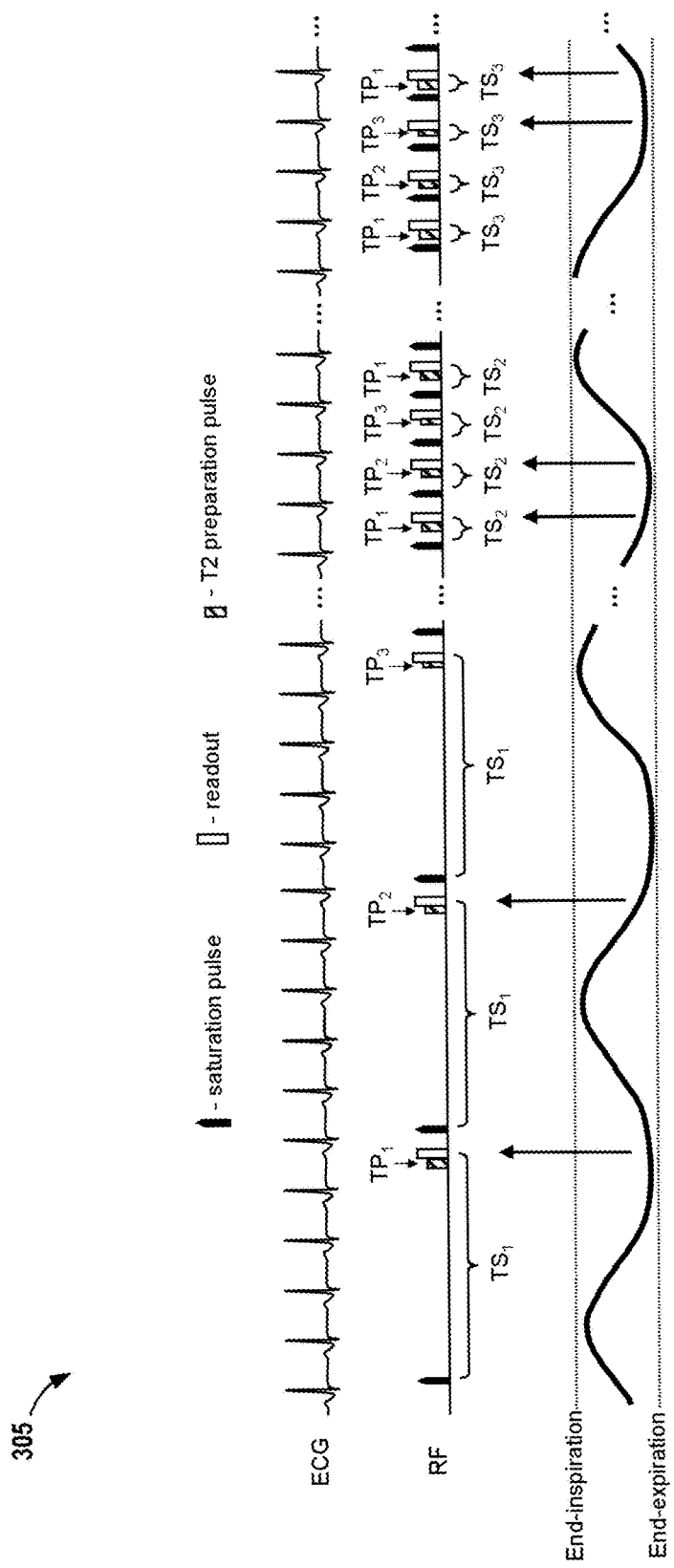
FIG. 3B illustrates an acquisition strategy where combined T1 and T2 mapping may be performed with three saturation times and three T2 preparation times, according to some embodiments.

Combined T1 and T2 mapping can be achieved by inserting T2 preparation pulses of variable duration between the saturation pulse and the readout at step 205 of FIG. 2. The T2 preparation pulses also serve to increase the contrast between the blood and myocardium, which is desirable for reliable motion correction. FIG. 3B illustrates an acquisition strategy 305 where combined T1 and T2 mapping may be performed with three saturation times and three T2 preparation times, according to some embodiments.

In some embodiments, image phase information can be utilized to improve motion correction, taking advantage of phase differences between flowing blood and relatively stationary myocardium, and the readout strategy can be modified to enhance this phase difference. For example, in one embodiment, a gradient associated with the readout is modified to enhance phase differences between flowing blood and stationary myocardium in the cardiac region.

Information from both the magnitude and phase images can be combined to improve image registration.

Figure 4:
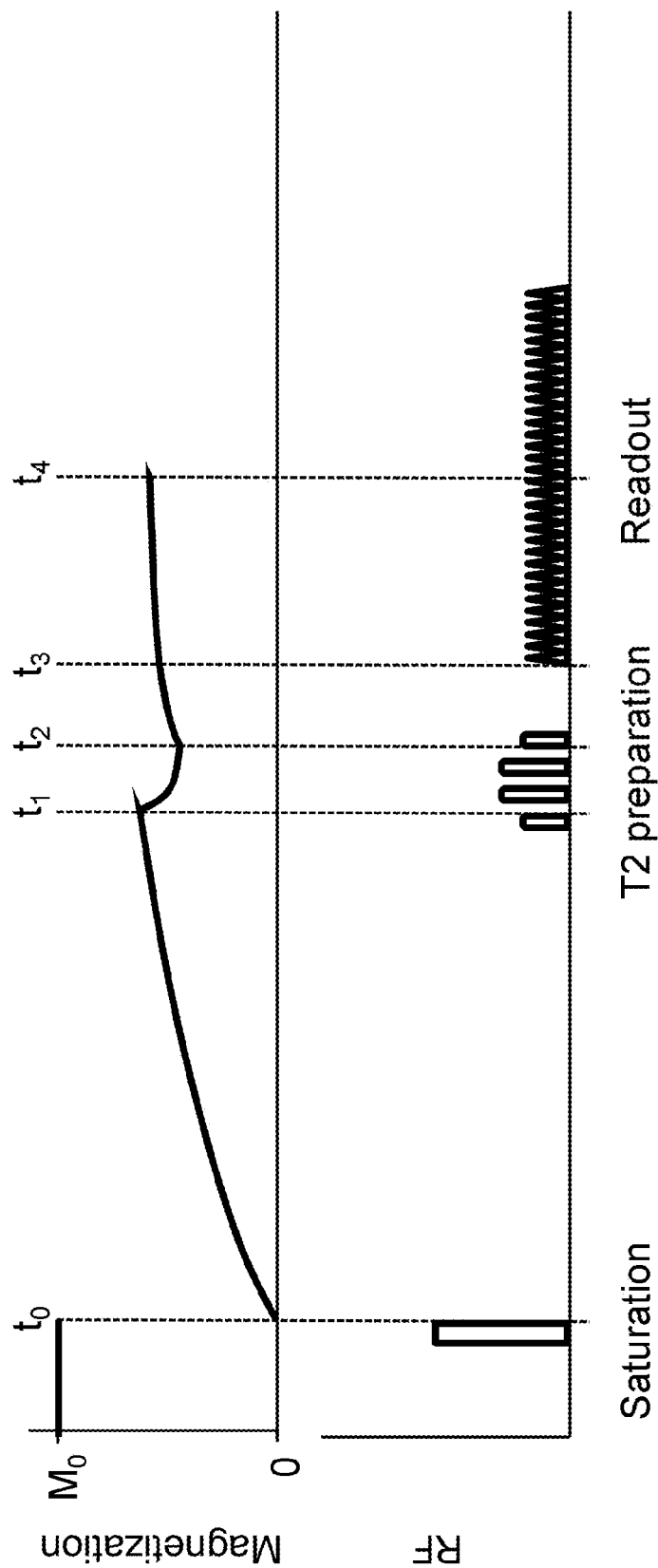
FIG. 4 shows the progression of magnetization for a saturation pulse, recovery period, T2 preparatory pulse, and single shot image readout that may be applied in some embodiments.

FIG. 4 shows the progression of magnetization for a saturation pulse, recovery period, T2 preparatory pulse, and single shot image readout that may be applied in some embodiments. The initial T2 recovery following the saturation pulse is given by:

$$M_{t1}=M_0(1-e^{-(t1-t0)/T1}), \quad (1)$$

where $M_0$ is the full longitudinal magnetization. Assuming no fluctuation of T1 between the tip down and tip up pulses in the T2 preparation module, the signal decay during this time period is defined by:

$$M_{t2}=M_{t1}e^{-(t2-t1)/T2}. \quad (2)$$

Following the T2 preparation module, there may be a gap to the beginning of the readout (e.g. tip up pulse and crushers), during which T1 recovery takes place:

$$M_{t3}=M_0-(M_0-M_{t2})e^{-(t3-t2)/T1}. \quad (3)$$

The readout may also be included, for example, with a balanced steady-state free precession (SSFP) readout with flip angle α:

$$M_{t4}=M_{SS}-(M_{SS}-M_{t3})e^{-(t3-t2)/T1}, \quad (4)$$

where $M_{SS}$ can be estimated using a Bloch calculation.

Depending on the acquisition scenario, some or all of all the above equations can be solved using a non-linear fit to $M_0$ and T1 (2 parameters), $M_0$, T1, and a bias term (3 parameters), or $M_0$, T1, T2 and a bias term (4 parameters). Alternatively, in some embodiments, iterative fitting is applied.

Figure 5:
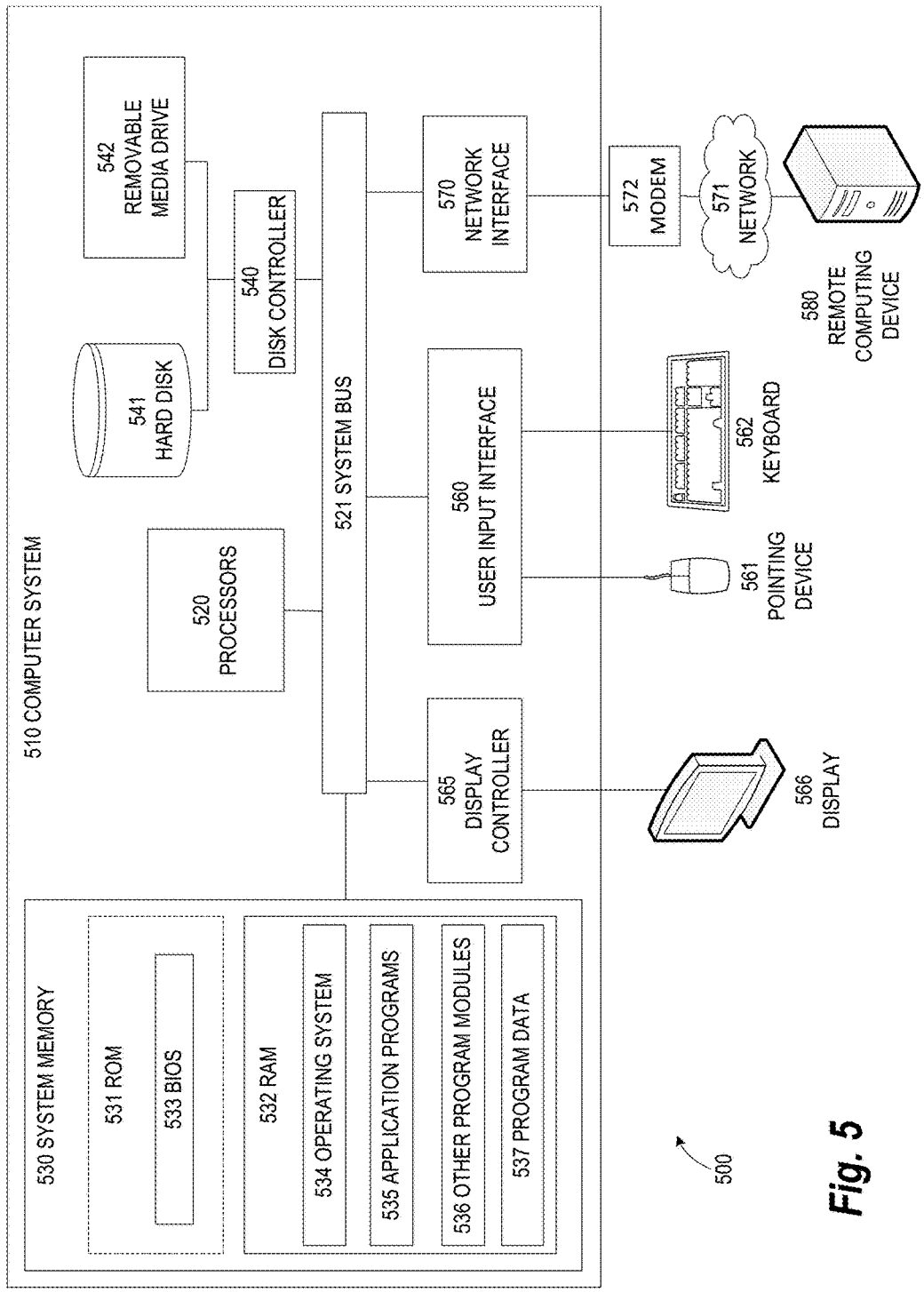
FIG. 5 illustrates an exemplary computing environment within which embodiments of the invention may be implemented.

FIG. 5 illustrates an exemplary computing environment 500 within which embodiments of the invention may be implemented. For example, this computing environment 500 may be used to implement the technique 200 described above with respect to FIG. 2. In some embodiments, the computing environment 500 may be used to implement one or more of the components illustrated in the system 100 of FIG. 1. The computing environment 500 may include computer system 510, which is one example of a computing system upon which embodiments of the invention may be implemented. Computers and computing environments, such as computer system 510 and computing environment 500, are known to those of skill in the art and thus are described briefly here.

As shown in FIG. 5, the computer system 510 may include a communication mechanism such as a bus 521 or other communication mechanism for communicating information within the computer system 510. The computer system 510 further includes one or more processors 520 coupled with the bus 521 for processing the information. The processors 520 may include one or more central processing units (CPUs), graphical processing units (GPUs), or any other processor known in the art.

The computer system 510 also includes a system memory 530 coupled to the bus 521 for storing information and instructions to be executed by processors 520. The system memory 530 may include computer readable storage media in the form of volatile and/or nonvolatile memory, such as read only memory (ROM) 531 and/or random access memory (RAM) 532. The system memory RAM 532 may include other dynamic storage device(s) (e.g., dynamic RAM, static RAM, and synchronous DRAM). The system memory ROM 531 may include other static storage device(s) (e.g., programmable ROM, erasable PROM, and electrically erasable PROM). In addition, the system memory 530 may be used for storing temporary variables or other intermediate information during the execution of instructions by the processors 520. A basic input/output system (BIOS) 533 containing the basic routines that help to transfer information between elements within computer system 510, such as during start-up, may be stored in ROM 531. RAM 532 may contain data and/or program modules that are immediately accessible to and/or presently being operated on by the processors 520. System memory 530 may additionally include, for example, operating system 534, application programs 535, other program modules 536 and program data 537.

The computer system 510 also includes a disk controller 540 coupled to the bus 521 to control one or more storage devices for storing information and instructions, such as a hard disk 541 and a removable media drive 542 (e.g., floppy disk drive, compact disc drive, tape drive, and/or solid state drive). The storage devices may be added to the computer system 510 using an appropriate device interface (e.g., a small computer system interface (SCSI), integrated device electronics (IDE), Universal Serial Bus (USB), or FireWire).

The computer system 510 may also include a display controller 565 coupled to the bus 521 to control a display 566, such as a cathode ray tube (CRT) or liquid crystal display (LCD), for displaying information to a computer user. The computer system includes an input interface 560 and one or more input devices, such as a keyboard 562 and a pointing device 561, for interacting with a computer user and providing information to the processor 520. The pointing device 561, for example, may be a mouse, a trackball, or a pointing stick for communicating direction information and command selections to the processor 520 and for controlling cursor movement on the display 566. The display 566 may provide a touch screen interface which allows input to supplement or replace the communication of direction information and command selections by the pointing device 561.

The computer system 510 may perform a portion or all of the processing steps of embodiments of the invention in response to the processors 520 executing one or more sequences of one or more instructions contained in a memory, such as the system memory 530. Such instructions may be read into the system memory 530 from another computer readable medium, such as a hard disk 541 or a removable media drive 542. The hard disk 541 may contain one or more datastores and data files used by embodiments of the present invention. Datastore contents and data files may be encrypted to improve security. The processors 520 may also be employed in a multi-processing arrangement to execute the one or more sequences of instructions contained in system memory 530. In alternative embodiments, hard-wired circuitry may be used in place of or in combination with software instructions. Thus, embodiments are not limited to any specific combination of hardware circuitry and software.

As stated above, the computer system 510 may include at least one computer readable medium or memory for holding instructions programmed according to embodiments of the invention and for containing data structures, tables, records, or other data described herein. The term "computer readable medium" as used herein refers to any medium that participates in providing instructions to the processor 520 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 541 or removable media drive 542. Non-limiting examples of volatile media include dynamic memory, such as system memory 530. Non-limiting examples of transmission media include coaxial cables, copper wire, and fiber optics, including the wires that make up the bus 521. Transmission media may also take the form of acoustic or light waves, such as those generated during radio wave and infrared data communications.

The computing environment 500 may further include the computer system 510 operating in a networked environment using logical connections to one or more remote computers, such as remote computer 580. Remote computer 580 may be a personal computer (laptop or desktop), a mobile device, a server, a router, a network PC, a peer device or other common network node, and typically includes many or all of the elements described above relative to computer system 510. When used in a networking environment, computer system 510 may include modem 572 for establishing communications over a network 571, such as the Internet. Modem 572 may be connected to bus 521 via user network interface 570, or via another appropriate mechanism.

Network 571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 510 and other computers (e.g., remote computer 580). The network 571 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 571.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method for performing free breathing pixel-wise myocardial T1 parameter mapping, the method comprising:
   performing a free-breathing scan of a cardiac region at a plurality of varying saturation recovery times to acquire a k-space dataset;
   generating an image dataset based on the k-space dataset;
   performing a respiratory motion correction process on the image dataset, the respiratory motion correction process comprising:
   selecting a target image from the image dataset,
   co-registering each image in the image dataset to the target image to determine a spatial alignment measurement for each image, and
   identifying a subset of the image dataset comprising images with the spatial alignment measurement above a predetermined value;
   following the respiratory motion correction process, performing a pixel-wise fitting on the image dataset to estimate T1 relaxation time values for the cardiac region;
   producing a pixel-map of the cardiac region depicting the T1 relaxation time values.

2. The method of claim 1, wherein the k-space dataset of the cardiac region comprises a plurality of redundant datasets for each of the plurality of varying saturation recovery times.

3. The method of claim 1, wherein the pixel-wise fitting performs a 2 parameter fit using a full longitudinal magnetization value and a T1 value.

4. The method of claim 1, wherein the pixel-wise fitting performs a variable order parameter fit using parameters comprising a full longitudinal magnetization value, a T1 value, and a bias term value.

5. The method of claim 1, wherein the free-breathing scan is performed using a saturation recovery T1 sampling strategy which applies a sequence comprising a saturation pulse and a readout repeated over a plurality of heartbeats.

6. The method of claim 5, further comprising:
modifying a gradient associated with the readout to enhance phase differences between flowing blood and stationary myocardium in the cardiac region;
generating a phase map based on the phase differences;
using the phase map in addition to the corresponding magnitude images to improve image co-registration.

7. The method of claim 5, wherein each sequence further comprises a T2 preparation pulse of variable duration inserted between the saturation pulse and the readout, and the method further comprises:
extending the pixel-wise fitting on the image dataset to additionally estimate T2 relaxation time values for the cardiac region; and
producing a second pixel-map of the cardiac region depicting the T2 relaxation time values.

8. The method of claim 7, wherein the T2 preparation pulse of variable duration is introduced immediately prior to the readout.

9. The method of claim 7, wherein the pixel-wise fitting performs a 4 parameter fit using parameters a full longitudinal magnetization value, a T1 value, a T2 value, and a bias term value.

10. The method of claim 7, wherein the T2 preparation pulse duration is kept constant to improve contrast between blood and myocardium.

11. A system for performing free breathing pixel-wise myocardial T1 parameter mapping, the article of manufacture comprising a non-transitory, tangible computer-readable medium holding computer-executable instructions for performing a method comprising:
using a magnetic resonance imaging scanner to perform a free-breathing scan of a cardiac region at a plurality of varying saturation recovery times to acquire a k-space dataset;
generating an image dataset based on the k-space dataset;
performing a respiratory motion correction process on the image dataset, the respiratory motion correction process comprising:
selecting a target image from the image dataset,
co-registering each image in the image dataset to the target image to determine a spatial alignment measurement for each image, and
identifying a subset of the image dataset comprising images with the spatial alignment measurement above a predetermined value;
following the respiratory motion correction process, performing a pixel-wise fitting on the image dataset to estimate T1 relaxation time values for the cardiac region; and
producing a pixel-map of the cardiac region depicting the T1 relaxation time values.

12. The system of manufacture of claim 11, wherein the k-space dataset of the cardiac region comprises a plurality of redundant datasets for each of the plurality of varying saturation recovery times.

13. The system of manufacture of claim 11, wherein the pixel-wise fitting performs a 2 parameter fit using a full longitudinal magnetization value and a T1 value.

14. The system of manufacture of claim 11, wherein the pixel-wise fitting performs a variable order parameter fit using parameters comprising a full longitudinal magnetization value, a T1 value, and a bias term value.

15. The system of manufacture of claim 11, wherein the free-breathing scan is performed using a saturation recovery T1 sampling strategy which applies a sequence comprising a saturation pulse and a readout repeated over a plurality of heartbeats.

16. The system of manufacture of claim 15, further comprising:
modifying a gradient associated with the readout to enhance phase differences between flowing blood and stationary myocardium in the cardiac region;
generating a phase map based on the phase differences;
using the phase map in addition to the corresponding magnitude images to improve image co-registration.

17. The system of manufacture of claim 15, wherein each sequence further comprises a T2 preparation pulse of variable duration inserted between the saturation pulse and the readout, and the method further comprises:
extending the pixel-wise fitting on the image dataset to additionally estimate T2 relaxation time values for the cardiac region; and
producing a second pixel-map of the cardiac region depicting the T2 relaxation time values.

18. The system of manufacture of claim 17, wherein the T2 preparation pulse of variable duration is introduced immediately prior to the readout.

19. The system of manufacture of claim 17, wherein the pixel-wise fitting performs a 4 parameter fit using parameters a full longitudinal magnetization value, a T1 value, a T2 value, and a bias term value.

20. A system for performing free breathing pixel-wise myocardial T1 parameter mapping, the system comprising:
a magnetic resonance imaging scanner configured to perform a free-breathing scan of a cardiac region at a plurality of varying saturation recovery times to acquire a k-space dataset;
a computer comprising an image data processor configured to:
generate an image dataset based on the k-space dataset;
perform a respiratory motion correction process on the image dataset, the respiratory motion correction process comprising:
selecting a target image from the image dataset,
co-registering each image in the image dataset to the target image to determine a spatial alignment measurement for each image, and
identifying a subset of the image dataset comprising images with the spatial alignment measurement above a predetermined value;
following the respiratory motion correction process, perform a pixel-wise fitting on the image dataset to estimate T1 relaxation time values for the cardiac region;
produce a pixel-map of the cardiac region depicting the T1 relaxation time values.

21. The system of claim 20, wherein:
the magnetic resonance imaging scanner is further configured to apply a plurality of T2 preparation pulses of variable duration between saturation pulses and readouts during the free-breathing scan of the cardiac region applies; and the image data processor is further configured to:
extend the pixel-wise fitting on the image dataset to additionally estimate T2 relaxation time values for the cardiac region; and
produce a second pixel-map of the cardiac region depicting the T2 relaxation time values.

* * * * *